United States Patent [19]

Potts, Jr.

[11] 4,205,014

[45] May 27, 1980

[54] PROCESS FOR 1,2,4,5-TETRACHLOROBENZENE

[75] Inventor: Irvin W. Potts, Jr., Midland, Mich.

[73] Assignee: The Dow Chemical Company, Midland, Mich.

[21] Appl. No.: 34,785

[22] Filed: Apr. 30, 1979

Related U.S. Application Data

[63] Continuation-in-part of Ser. No. 869,562, Jan. 16, 1978.

[51] Int. Cl.$^2$ ............................................. C07C 25/00
[52] U.S. Cl. ............................. 260/650 R; 252/429 R
[58] Field of Search .................................... 260/650 R

[56] References Cited

U.S. PATENT DOCUMENTS 3,557,227   1/1971   Fooladi ........................... 260/650 R

*Primary Examiner*—Delbert E. Gantz
*Assistant Examiner*—Joseph A. Boska
*Attorney, Agent, or Firm*—G. R. Plotecher

[57] ABSTRACT

The process for preparing 1,2,4,5-tetrachlorobenzene, the process comprising contacting at reactive conditions 1,2,4-trichlorobenzene and chlorine gas in the presence of a catalytic amount of at least one Lewis acid, such as ferric trichloride, is improved by using as a cocatalyst a polymeric compound having a plurality of iodinated benzene nuclei, such as an iodinated polystyrene resin.

8 Claims, No Drawings

PROCESS FOR 1,2,4,5-TETRACHLOROBENZENE

CROSS-REFERENCE TO RELATED APPLICATION

This is a continuation-in-part of our copending application Ser. No. 869,562, filed Jan. 16, 1978.

BACKGROUND OF THE INVENTION

1. Field of the Invention:

This invention relates to an improved process for preparing 1,2,4,5-tetrachlorobenzene.

2. Description of the Prior Art:

The production of 1,2,4,5-tetrachlorobenzene from a Lewis acid-catalyzed contacting of 1,2,4-trichlorobenzene and chlorine gas is known. However, for each pound of desired isomer produced, about 0.5 pounds of undesired isomers and tars are also produced. This latter material has little or no utility whereas the former material is a precursor of 2,4,5-trichlorophenol, an intermediate to many valuable, biologically active compounds. Any improvement in the yield of the 1,2,4,5-isomer is therefore desirable.

SUMMARY OF THE INVENTION

According to this invention, the process for preparing 1,2,4,5-tetrachlorobenzene, the process comprising contacting at reactive conditions 1,2,4-trichlorobenzene and chlorine gas in the presence of a catalytic amount of at least one Lewis acid is improved by using as a catalyst at least one polymeric compound having a plurality of iodinated benzene nuclei. This cocatalyst system demonostrates enhanced regioselectivity for 1,2,4,5-tetrachlorobenzene (as compared to systems of Lewis acids alone), thus reducing the formation of other tetra isomers and tar.

DETAILED DESCRIPTION OF THE INVENTION

The polymeric compounds of this invention typically have a sufficient number of iodinated benzene nuclei that the iodine content of any given compound, based on its weight, is at least about 10 percent and preferably at least about 25 percent. Practical considerations are the only limitations on the maximum number of iodinated benzene nuclei there polymeric compounds can have but for reasons of economy and convenience, typically the maximum number is such that the iodine content of any given compound does not exceed about 60 weight percent and preferably does not exceed about 50 weight percent.

The iodinated benzene nuclei of these polymeric compounds can be either pendant to or integral with the polymer backbone. An example of the former is an iodinated polystyrene resin while an example of the latter is an iodinated diphenyl ether-formaldehyde resin. When a nucleus is pendant to the backbone, the iodo moiety is preferably para to the bond attaching the nucleus to the backbone.

In addition to the iodo moiety, the benzene nuclei can also bear up to three substituents which have less affinity for electrons than does hydrogen. These substituents can be ortho, meta and/or para to the iodo moiety but those nuclei bearing a substituent preferably bear it in the para position (presuming, of course, that that position is available, i.e. it is not the position at which the nuclei are attached to the remainder of the polymer). Preferred substituents can be further defined as having a Hammett sigma value of less than about −0.1 (wherein the sigma value is determined by using a benzoic acid ionization standard as described by E. S. Gould, *Mechanism and Structure in Organic Chemistry*, p. 221, Holt, Reinhart & Winstron (N.Y. 1959)). Typical substituents include alkyl, such as methyl, ethyl, propyl, isopropyl, pentyl, neopentyl, decyl, etc.; alkoxy, such as methoxy, ethoxy, propoxy, butoxy, etc.; halogen, such as chloride, bromide, iodide, etc.; amino, such as amine ($-NH_2$), methylamine, dimethylamine, ethylamine, diethylamine, etc.; aryl, such as phenyl, tolyl, xylyl, etc. and the like. $C_1-C_6$ alkyl and $C_1-C_6$ alkoxy are the preferred substituents and $C_1-C_6$ alkoxy are the most preferred substituents.

Representative polymeric compounds include those prepared from the iodination of such materials as cross-linked polystyrene beads, diphenyl oxide-formaldehyde resins, copolymers of styrene and such copolymerizable mononers as 1,3-butadiene, copolymers of monovinylidene aromatic monomers, etc. The iodinated polymers of cross-linked polystyrene and diphenyl oxide-formaldehyde resins are particularly preferred.

The polymeric compounds are used in combination with at least one Lewis acid catalyst. Any Lewis acid that can catalyze the chlorination of 1,2,4-trichlorobenzene can be here used. Illustrative Lewis acids include: manganese dichloride, zinc dichloride, titanium tetrachloride, tin tetrachloride, antimony trichloride, aluminum trichloride, ferric trichloride, ect. Lewis acids containing other halogen atoms, such as aluminum tribromide, ferric dibromochloride, etc. can also be here used but are generally disfavored because of possible halogen exchange with the starting materials (chlorinated benzenes) and resulting contamination of the product. Because of their superior catalytic activity, ferric, antimony and aluminum trichloride are preferred Lewis acids with ferric trichloride generally most preferred. The Lewis acids of this invention can be used per se or generated in situ.

Any combination of polymeric compound and Lewis acid that will demonostrate an enhanced regioselectivity for 1,2,4,5-tetrachlorobenzene can form the cocatalyst system of this invention. Typically, the cocatalyst system comprises one Lewis acid and one polymeric compound but cocatalyst systems comprising more than one Lewis acid and/or more than one polymeric compound can also be used. The respective amounts of Lewis acid(s) and polymeric compound(s) in the cocatalyst system will vary with individual combinations but combinations having a minimum equivalents of polymer-bound iodine:equivalents of Lewis acid ratio of about 0.5:1 are preferred, with a minimum equivalents ratio of about 1:1 most preferred. The preferred maximum equivalents ratio is about 4:1, with a maximum equivalents ratio of 2:1 most preferred. The polymeric compound must be used in combination with the Lewis acid because unlike the Lewis acid, the polymeric compound alone will not catalyze the chlorination of 1,2,4-trichlorobenzene.

A catalytic amount of the cocatalyst system is used in the chlorination of 1,2,4-trichlorobenzene to 1,2,4,5-tetrachlorobenzene. Typically, a minimum amount of about 0.2 mole percent (based upon the 1,2,4-trichlorobenzene) of cocatalyst system (moles of polymeric compound calculated on iodine equivalents) is used and preferably about 0.4 mole percent. Practical considerations, such as convenience, economy, etc., are the only limitations upon the maximum amount of cocatalyst system that can be employed, but generally a maximum of about 1 mole percent, and preferably of about 0.8 mole percent, is used.

The cocatalyst system of this invention is used in the same manner as the Lewis acid catalyst is used in the known process for preparing 1,2,4,5-tetrachlorobenzene from 1,2,4-trichlorobenzene. Typically, in the presence of a cocatalyst system, chlorine gas is bubbled into the starting material which contains 1,2,4,-trichlorobenzene but generally also contains benzene, chlorobenzene, dichlorobenzenes and other trichlorobenzene isomers. Some of these other starting materials are eventually converted to 1,2,4-trichlorobenzene during the course of the process. The starting material is maintained at reactive conditions which can vary with the cocatalyst system employed. Where cocatalyst systems comprising antimony, aluminum or ferric trichloride are used, conditions generally between about 40° C. and 120° C., and preferably between about 60° C. and about 90° C. are employed. Atmospheric pressure is typically employed although superatomospheric pressure can also be used if desired. Further description of the conventional chlorination process is given by Fooladi, U.S. Pat. No. 3,557,227.

The following examples are illustrative embodiments of this invention. Unless indicated to the contrary, all parts and percentages are by weight.

EXAMPLES 1-3

Polymer Preparation

Polystyrene beads (56 g) cross-linked with 8 percent divinylbenzene, iodine (63.45 g) and perchloroethylene (200 ml) were charged to a three-neck flask equipped with a dropping funnel, stirrer, thermometer and condenser. The dropping funnel was filled with nitric acid (100 ml. 70 percent) and the flask heated to about 100° C. with an infrared heating lamp. The nitric acid was added dropwise over a period of 4 hours and then the resulting mixture was post-reacted for an additional hour. Nitrogen was bubbled through the mixture to remove residual hydrogen iodide and nitrogen oxides. The iodinated resin was removed by filtration and sequentially washed with 400 ml of 8 percent sodium hydroxide, 500 ml of water and 1000 ml of perchloroethylene. The resin was then dried overnight in a vacuum oven at 30 inches Hg and 60° C. Analyses of this resin showed that it contained 45.5±0.9% iodine, 6±1% chlorine and 0.73–0.87% nitrogen. This resin is designated "Catalyst A" in Table I.

A diphenyl oxide-formaldehyde polymer was iodinated in a manner analogous to the polystyrene beads. Polymer (79.4 g) and iodine (55 g) were added to perchloroethylene (200 ml) with the subsequent addition over 6 hours of nitric acid (100 ml, 70 percent). The resulting iodinated polymer was then removed by filtration, washed and dried overnight. Analysis: 27.5±0.5% iodine; 1.08% nitrogen. This resin is designated "Catalyst B" in Table I.

Chorination of 1,2,4-Trichlorobenzene

Catalyst resin (2 g) and anhydrous ferric trichloride (0.375 g) were added to 1,2,4-trichlorobenzene (250 g). The resulting reaction mixture was then heated to the desired temperature and subsequently sparged with chlorine. Samples were periodically removed, washed with saturated sodium carbonate solution, dried over anhydrous sodium sulfate and analyzed by gas chromatography. The results are reported in Table I.

As a basis of comparison, the use in the above-described procedure of ferric trichloride alone generates a 1,2,4,5-/1,2,3,4-tetrachlorobenzene mole ratio of about 1.

TABLE I
CHLORINATION OF 1,2,4-TRICHLOROBENZENE WITH A FERRIC CHLORIDE-POLYMERIC COMPOUND COCATALYST SYSTEM

| Ex. | Catalyst | Temperature (°C.) | Mole % Composition at Freezing Point[1] | | | | Ratio[3] |
|---|---|---|---|---|---|---|---|
| | | | 1,2,4 | 1,2,4,5 | 1,2,3,4 | Penta[2] | |
| 1 | A | 40 | 82.51 | 12.58 | 4.65 | — | 2.7 |
| 2 | A | 40 | 67.16 | 23.27 | 9.18 | 0.34 | 2.5 |
| 3 | B | 45 | 80.00 | 13.89 | 5.73 | 0.14 | 2.4 |

[1]Freezing point of the mixture at the specified temperature.
[2]Pentachlorobenzene.
[3]1,2,4,5-/(1,2,3,4-tetrachlorobenzene + penta) mole ratio.

The preceding examples were for illustrative purposes only and are not to be construed as limitations upon the invention. The skilled artisan will recognize that many variations can be made on this invention without departing from the spirit and scope of the appended claims.

What is claimed is:

1. In the process of preparing 1,2,4,5-tetrachlorobenzene, the process comprising contacting at reactive conditions 1,2,4-trichlorobenzene and chlorine gas in the presence of a catalytic amount of Lewis acid, the improvement comprising using as a cocatalyst at least one polymeric compound having a plurality of iodinated benzene nuclei.

2. The process of claim 1 wherein the polymeric compound has a sufficient number of iodinated benzene nuclei that the iodine content of the compound is at least about 10 weight percent.

3. The process of claim 1 wherein the polymeric compound has a sufficient number of iodinated benzene nuclei that the iodine content of the compound is at least about 25 weight percent.

4. The process of claim 3 wherein the polymeric compound is prepared from the iodination of cross-linked polystyrene beads or a diphenyl oxide-formaldehyde resin.

5. The process of claim 4 wherein the polymeric compound and Lewis acid are present at an equivalents of polymer-bound iodine:equivalents of Lewis acid ratio of about 0.5:1 to about 4:1.

6. The process of claim 5 wherein the Lewis acid is ferric trichloride.

7. The process of claim 6 wherein the cocatalyst system of Lewis acid and polymeric compound is present in an amount of about 0.2 to about 1 mole percent based upon the 1,2,4-trichlorobenzene.

8. The process of claim 7 wherein the reactive conditions are a temperature between about 40° C. and about 120° C. and about atmospheric pressure.

* * * * *